US006342395B1

(12) United States Patent
Hammock et al.

(10) Patent No.: US 6,342,395 B1
(45) Date of Patent: Jan. 29, 2002

(54) COMPACT ASSAY SYSTEM WITH DIGITAL INFORMATION

(75) Inventors: Bruce D. Hammock; Horacio Kido, both of Davis, CA (US); Angel Maquieira, Valencia (ES)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/064,387

(22) Filed: Apr. 22, 1998

(51) Int. Cl.⁷ ............................................. G01N 33/543
(52) U.S. Cl. ........................ 436/518; 422/50; 422/55; 422/64; 422/67; 422/82.05; 422/82.11; 422/99; 435/6; 435/7.1; 435/7.5; 435/7.94; 435/7.93; 436/523; 436/172; 436/805; 436/809; 204/406
(58) Field of Search ............................... 422/50, 55, 64, 422/67, 82.05, 82.11, 99; 435/6, 7.1, 7.5, 7.93, 7.94; 436/518, 523, 172, 805, 809; 204/406

(56) References Cited

U.S. PATENT DOCUMENTS

| | | | |
|---|---|---|---|
| 5,136,572 A | * | 8/1992 | Bradley |
| 5,254,477 A | | 10/1993 | Walt |
| 5,451,683 A | | 9/1995 | Barrett et al. |
| 5,482,867 A | | 1/1996 | Barrett et al. |
| 5,494,829 A | | 2/1996 | Sandstrom et al. |
| 5,516,635 A | | 5/1996 | Ekins et al. |
| 5,545,531 A | * | 8/1996 | Rava et al. |
| 5,552,272 A | | 9/1996 | Bogart |
| 5,578,832 A | | 11/1996 | Trulson et al. |
| 5,629,214 A | | 5/1997 | Crosby |
| 5,639,671 A | | 6/1997 | Bogart et al. |
| 5,641,634 A | * | 6/1997 | Mandecki |
| 5,658,802 A | | 8/1997 | Hayes et al. |
| 5,922,617 A | * | 7/1999 | Wang et al. |
| 5,935,785 A | * | 8/1999 | Reber et al. |
| 6,017,496 A | * | 1/2000 | Nova et al. |
| 6,090,558 A | * | 7/2000 | Butler et al. |

OTHER PUBLICATIONS

Bell, Alan E., "Next–Generation Compact Discs," *Scientific American* (Jul. 1996), pp. 42–46.

Gunshor et al., "Blue–Laser CD Technology," *Scientific American* (Jul. 1996), pp. 48–51.

Harley et al., "CD ROM Manufacturing," Chapter 15 in *The CD ROM Handbook*, ed. Sherman, Chris, New York: Intertext Publications, McGraw–Hill Book Company (1988) pp. 419–434.

Kearl and Ard, "Low–Cost Plain–Paper Color Inkjet Printing," *Hewlett–Packard Journal* (Aug. 1992), pp. 64–68.

Nilsson et al., "Thin–Layer Immunoaffinity Chromatography with Bar Code Quantitation of C–Reactive Protein," *Anal. Chem.*, 67 (1995), pp. 3051–3056.

(List continued on next page.)

*Primary Examiner*—Bao-Thuy L. Nguyen
(74) *Attorney, Agent, or Firm*—Knobbe, Martens, Olson & Bear, LLP

(57) ABSTRACT

A compact assay system having a solid support has at least one capture binding agent on the support surface. By applying a combination of different binding agents on the support surface, the present invention can conduct multiple chemical reactions on the support solid support to detect analytes of interest. The specific reagents, or capture binding agents, are preferably immobilized on the solid support by means of a computer controlled, miniaturized printing system. Specifically, the reagents can be applied onto the solid support using a commercial available printhead of an ink-jet printer. In addition, the support surface also includes areas adapted to be digitally readable by laser to store information concerning binding between capture agents and analytes.

4 Claims, 4 Drawing Sheets

OTHER PUBLICATIONS

Rosewarne, Kathleen, "Low–Cost Ink–Jet Printing," *Physics World* (Aug. 1990), p. 21.

Nadler and Wiesenberg, "CD ROM Hardware," Chapter 4 in *The CD ROM Handbook*, ed. Sherman, Chris, New York: Intertext Publications, McGraw–Hill Book Company (1988), pp. 79–106.

Williams et al., "Instrument to Detect Near–Infrared Fluorescence in Solid–Phase Immunoassay," *Anal. Chem.*, 66 (1994), pp. 3102–3107.

Product literature of "Storm"™ gel and blot imaging system, by Molecular Dynamics (1995).

Entire issue of *Hewlett–Packard Journal*, vol. 36, No. 5 (May 1985), pp. 1–40.

Maze et al., "Ink and Print Cartridge Development for the HP DeskJet 500C/Desk Writer C Printer Family," *Hewlett–Packard Journal* (Aug. 1992), pp. 69–76.

* cited by examiner

COMPACT ASSAY SYSTEM WITH DIGITAL INFORMATION

This invention was made with Government support under Grant Nos. ES 07059, ES04699, and ES05707, awarded by the National Institutes of Health, and Grant No. CR819658, awarded by the Environmental Protection Agency. The Government has certain rights in this invention.

FIELD OF THE INVENTION

This invention generally relates to immobilized anti-ligands, and more particularly relates to a solid support having immobilized anti-ligands thereon, which is useful in generating information in analog form about multianalytes of interest, and which further carries information in digital form related to the multianalyte detection on the same support. Preferred solid support embodiments are compact discs with miniaturized quantities of reagents applied by piezoelectric jet on one side, and pit and land formations on the other side that are digitally readable by laser.

BACKGROUND OF THE INVENTION

Clinical and diagnostic assays can be relatively expensive to perform, involve wasted reagents (e.g. patient blood), and are limited in the number of multianalytes run. Particularly where one wishes to perform a large number of assays, such as for environmental monitoring, the present tools for conducting these analyses have posed problems of cost and inefficiencies.

Antibody immobilization on thin-layer immunoaffinity chromatography membranes through use of a modified piezoelectric driven ink-jet printer has recently been reported by Nilsson et al. in *Analytical Chemistry*, 67, pages 3051–3056 (1995). These immobilized antibodies can be in the form of several bands with different amounts of antibodies for quantitative measurement of the antigen of interest.

Ekins and Chu in U.S. Pat. No. 5,516,635, issued May 14, 1996, describe a solid support with microspots with which labeled microspheres are used to perform immunoassays. The strength of signal from the labels is representative of the fractional occupancy of binding sites.

U.S. Pat. No. 5,494,829, issued Feb. 27, 1996, Sandstrom et al., and U.S. Pat. No. 5,552,272, issued Sept. 3, 1996, Bogart, describe optical supports which are said to have an enhanced level of exciting photons to immobilize fluorescent labels. The optical substrates produce different colors related to the thickness of a film.

Thus, advances in the technology for immobilization of reagents, particularly through miniaturization and increased automation of detection, are being made. Nevertheless, a need remains for highly automated assay devices, useful for environmental monitoring, clinical screening, and the like, which can be performed efficiently at reasonable cost.

SUMMARY OF THE INVENTION

In one aspect of the present invention, a solid support is provided that has at least one capture binding agent on a support surface. The support surface also includes areas adapted to be digitally readable by laser when information is carried thereon. In addition or as an alternative, these informational areas are adapted to be digitally writable by laser so as to carry selected information thereon. Such information is preferably carried via a plurality of microscopic pit and land formations. In use, the inventive supports can store information concerning binding between capture binding agents and analytes.

Particularly preferred support embodiments of the invention are optical compact discs that carry specific reagents capable of binding with multiple analytes. The specific reagents, or capture binding agents, are preferably immobilized on the discs by means of a computer controlled, miniaturized printing system. These support embodiments are useful in conducting chemical reactions to detect analytes of interest and to read and/or store electronic information, for example, electronic information that records the assay results, on the support itself by use of a laser.

In another aspect of the present invention, an apparatus is provided that comprises at least one piezoelectric head contained in a commercially available printhead of an ink jet printer. The printhead is removed from the printer and fixed on a disk drive's carriage sliding mechanism while remaining connected to the printer's printhead driver circuitry via a printer ribbon cable. Both the platter and sliding mechanism on the floppy disk drive assembly are controlled by a program via a digital interface card in the ISA port of the personal computer. By controlling the disk drive's carriage sliding mechanism, the piezoelectric head can be positioned at any specific position over the support surface to apply droplets of reagents on the support surface.

In another aspect of the present invention, the printhead comprises a plurality of piezoelectric heads. Each of the piezoelectric heads connects to a separate syringe cylinder containing a different reagent to be printed on the support surface. Therefore, a combination of different reagents can be applied to any position on the support surface.

DETAILED DESCRIPTION OF THE PREFERRED EMBODIMENTS

Figure 1:
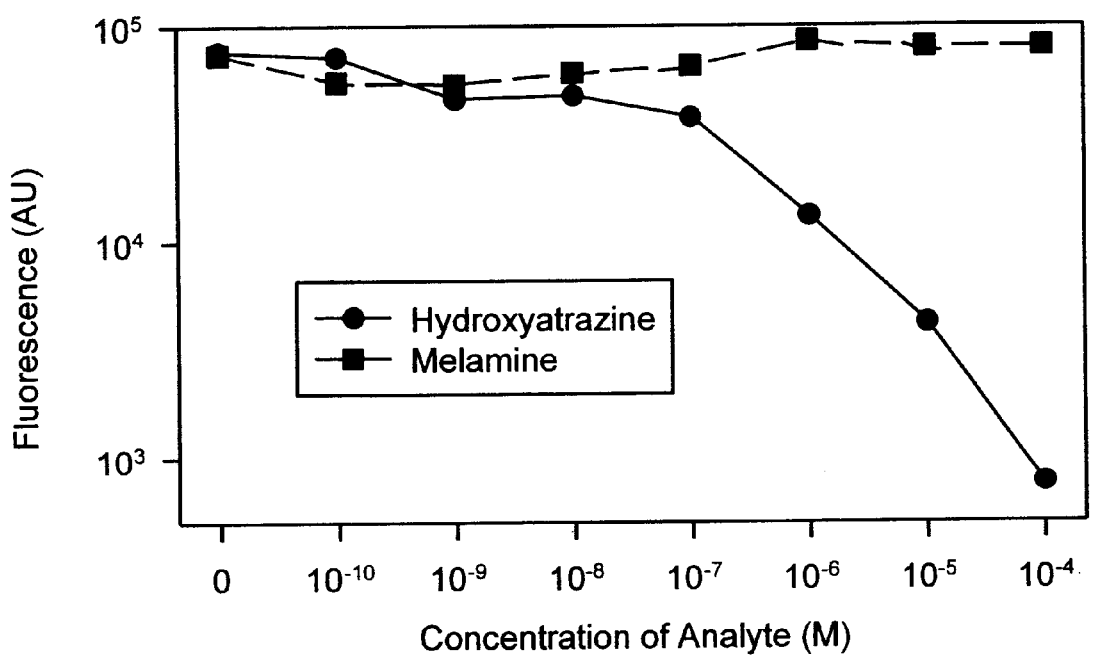
FIG. 1 graphically illustrates different concentrations of hydroxy-atrazine as a model target analyte, which were detected through a competitive assay conducted on a solid support embodiment of the invention, and by contrast melamine as a control.

A key component of the inventive compact assay system is the solid support. The solid support has immobilized anti-ligands on its surface and is digitally readable (or writable) with selected information.

Another aspect of the system is a miniaturized printing apparatus for immobilizing the selected anti-ligands (hereinafter also called "capture binding agents"). A preferred printing apparatus is whereby a piezoelectric head may be positioned at specific distances from the support and used to apply drops to the support surface. The support can be simultaneously rotatable at variable speeds so that the distance, or overlap, of the applied drops can be controlled arrays of either discrete dots or of lines. The support can be rotated with a step motor in order to control the angular deposition, with the piezoelectric jet head being perpendicular to the plane of the support. Its movement across the plane may be bidirectional so that a multiple ring pattern may be deposited. The piezoelectric head preferably has multiple reservoirs so as to store separate reagents to be sprayed onto the disc.

Although the miniaturized printing apparatus is preferred for immobilizing the capture binding agent on the support (typically by means of adsorption), other techniques and types of adherence to the support are feasible for practicing the invention. The solid support will first be described.

Solid Support and Preparation

The solid support includes informational surfaces that are adapted to be digitally readable by laser. Information on these surfaces is preferably carried by means of microscopic pit and land formations. For example, the informational surfaces can be provided by the use of conventional compact discs with already existing memory, or which can be recordable. The discs can be of various sizes. Present standards are diameters of 5¼ inches and 2 inches, both of which work on the same CD player spindle. Further, variations and subsequent generations of compact discs, such as those with a digital versatile disc (DVD) format, are contemplated and also suitable for use as the solid support.

When the solid support has readable information at the informational surfaces, then that information preferably is related to the presence or quantity of the analyte or analytes of interest. For example, the readable information can comprise analytical software for performing the desired detection or assays. Among the commercially available software for performing detection or assay steps useful in practicing this invention is the Softmax™ program available from Molecular Devices Incorporated.

Alternatively, tailor made software adapted to perform detection or analytical steps pertaining to the capture binding agents can be developed by the user. The tailor made software can control the printhead position over the support surface and perform data manipulation and interpretation. It can be written, for example, in BASIC, Pasal, or C computer programming languages. An example of the tailor made software written in BASIC computer language is provided with this application as Appendix A.

Where the information is recordable at the informational surfaces, then that information preferably concerns binding between the capture binding agent (or agents) and the analyte (or analytes) of interest. As is known, writable compact discs are similar to conventional playback discs in typically being composed of polycarbonate substrate, a metal reflective layer, and a protective top layer. However, writable media typically has sandwiched between the substrate and reflective layer a recording layer that is composed of an organic dye. A laser then is used to create a series of holes in the disc's dye layer so that the holes (or pits) and spaces between the pits (lands) have a pattern that encodes the information and allows it to be retrieved on a compact disc player.

Immobilization of Capture Binding Agent

The capture binding agent can be immobilized on the solid support by any of the known immobilization techniques. Attachment between the capture binding agent and solid support may be physical (e.g. adsorption) or chemical (e.g. covalent bonding). An example of the latter is by photolithography so that the capture binding agents are immobilized in selectively defined areas of the solid support. An illustrative such photolithography method is disclosed by U.S. Pat. No. 5,482,867, issued Jan. 9, 1996, inventors Barrett et al., in which a photoactivatable biotin is attached to the support, selected regions of the support are irradiated so as form activated regions, and the capture binding agent, which has been complexed with avidin, is then used so as to attach the capture binding agent via the avidin-biotin binding reaction.

An example by adsorption is whereby the capture binding agent is carried by a liquid during the deposition and the deposition is performed by ejecting the liquid through an ink-jet printhead, as will be more fully described hereinafter. Among the suitable capture binding agents are proteins which will adsorb to the support due to hydrophobic sites, enzymes, or the enzyme ligand partner (substrate or a fragment thereof so long as including a reaction site recognized by the enzyme), immunoglobulins and their binding partners, or at least a fragment with an antigenic determinant for the immunoglobulin. Molecules of interest for the capture binding agent that do not readily adsorb, such as oligosaccharides (lectins), oligonucleotides, hormones, and the like can be attached by covalent bonding. Indeed, the preferred ink-jet method of deposition can be still be utilized for the non-adsorbing molecules by preactivating the solid surface.

There are several preactivating methods for different surface types. Most of these preactivating methods involve generation of surface electrophilic moieties to react with the nucleophilic functional groups on the target molecules to make a covalent bond. For example, in the polystyrene surface, graft copolymer process is used in which psoralen derivatives are chemically attached to the support surface by a UV-catalyzed free radical reaction. The detailed immobilization process is described by Hermanson, G. T., Mallia, A. K., and Smith, P. K. in *Immobilized Affinity Ligand Techniques,* Academic Press, Inc., 1992, San Diego, Calif., and hereby incorporated by reference. In the present invention, up to $10^{14}$ functional molecules per square centimeter can be generated by this method.

Capture Binding Agent Capacity and Arrays

A plurality of capture binding agents is preferably immobilized on the inventive support so as to detect multiple analytes of interest. For example, in current medical diagnostic procedures, panels for multiple analytes are frequently run. Thus, it would be useful (and the present invention provides) running multiple analyte detection for medical diagnostic applications including: HIV, Hepatitis, Prostate-Specific Antigen (PSA), and Creatine Kinase, etc.

The capture binding agents may be immobilized in substantially any pattern of dots or curves. The capacity of the inventive supports is great. With a piezoelectric printing head, and assuming a free space on a standard CD disc of over 3 cm and a separation between dots of 100 $\mu$m per dot, one can apply about 1,500 dots per circle and 150 circles per disc. This amounts to 225,000 spots. Using for example 15 dots per analyte, this means one is theoretically able to detect about 15,000 different compounds on only a surface of 21 cm$^2$. By contrast, the typical EIA kit uses microtiter plates with only 96 wells.

Repeated applications of capture binding agent at the same location increase the concentration of the agent and can produce a different signal for an analyte, which consequently allows for quantification. It is also possible to develop a concentration gradient for one or more of the capture binding agents immobilized on the surface. It is therefore preferred to spatially define, or precisely index, the dots, lines, and so forth one is using so that an additional layer can be readily accomplished.

Types of Assays

A wide variety of assays are feasible with the inventive supports, such as competitive, non-competitive, direct, indirect, sandwich, and so forth.

For example, in competitive immunoassay format, each of the following three configurations can be used.

1. First, an antianalyte antibody is directly immobilized onto the support surface. Then free target analytes and labeled haptens are introduced to compete for available antibody sites to form the assays.
2. A special anti-immunoglobulin antibody is first immobilized on the surface. Then antianalyte antibodies are introduced and trapped by the immobilized antibodies so that free target analytes and labeled haptens can compete for the available antibody sites.
3. Haptens are introduced and immobilized by covalently linked to proteins. The resulting conjugates are then adsorbed onto the surface so that the immobilized haptens can compete with free analytes for any available labeled anti-analyte antibodies. A variant of this format utilizes non-labeled anti-analyte antibodies followed by labeled anti-immunoglobulin antibodies.

Another example of the present invention is the non-competitive format. The most common immunoassay of the non-competitive format is the two-site (sandwich) immunoassay. Analyte is first captured by an immobilized antibody which recognizes one eptiope on the analyte. A second antibody which is labeled then recognizes and attaches to a second spetiope on the immobilized analyte to form the sandwich.

Spatially-resolved assays are particularly desirable whereby specific capture binding agents are immobilized on exactly defined reaction areas of the support, having for example, approximately 100 $\mu$m of diameter or width, by using the computer controlled printing system that will be more fully described hereinafter. The concentration of capture binding agent is chosen so that the fractional occupancy of binding sites is related to the concentration of the analyte or analytes in the sample. Fractional occupancy is assessed by the measurement of tracer signal intensity using only one general label.

The capture binding agents on the supports have the capacity to form a complex with the target analytes. The complex is formed due to a high binding affinity between the immobilized agent and the corresponding target analyte. The bound analyte can be detected through a property that changes when the complex is formed, for example fluorescent polarization, or can be detected indirectly by using labeled reagents.

Examples of suitable capture binding agents are antigens, hapten-protein conjugates, antibodies, protein A or protein C, hormones, metal chelators, enzymes, derivatized gold particles, oligosaccharides, DNA, oligonucleotides or fragments. In general, any substance having a high binding capacity and specificity for another is potentially suitable as the capture binding agent. For example, among capture binding agents are an antibody bound to protein A, a surface cell receptor for a hormone, an oligonucleotide sequence to its complementary DNA or RNA sequence, concanavalin A to mannose, etc. Immobilization of enzymes or their corresponding substrates can also be used.

Labels

Various detection systems and apparatus can be used for performing assays using the inventive supports. The labels will typically give an optical signal or a quenched, existing optical reading. Preferred labels are fluorescers, and particularly preferred are uses of light sensitive dyes at a near IR wavelength, such as about 790 nm. However, suitable are, for example, Cy5, Cy5.5, Cy7, La Jolla Blue, NN382, europeum chelates, terbium chelates, platinum coproporphyrin, or palladium coproporphyrin.

In performing an ELISA, for example, the capture binding agent may be antigen specific antibody which, when a fluid sample containing the suspected antigen is contacted, will bind. A second antibody with an enzyme label is added followed by a fluorochrome or chromogenic substrate. These various methods for determining an analyte of interest from an immobilized capture binding agent are well known to persons skilled in the art.

Aspects of the invention will now be illustrated by the following examples, which are intended to exemplify, but not limit, the invention.

EXAMPLE 1

Preparation of the Supports

The supports are preferably degreased in a suitable washing solution, such as polyoxyethylene-sorbitan monolaurate (Tween 20) at 5% v/v in water. The discs may be treated for 10 minutes by soaking, followed by rinsing with water and spinning the supports at 1000 rpm while directly adding deionized water. The support surface is then preferably activated for receptivity to an immobilization step, such as by being immersed in methanol (100%) for 15 minutes, and then spun at 1000 rpm 3 minutes at room temperature. Once preactivated, the supports are preferably stored in dried containers under vacuum to be kept free of dust until capture binding agent is applied.

The support surface on which is carried the immobilized capture binding agents is preferably non-reflective (such as a flat black) to avoid background interference when generating a chemical signal such as fluorescence during detection of analyte information.

EXAMPLE 2

Working with the CD disc activated as described by Example 1, different reagents were deposited on the surface using a micropipette. Conjugates of protein-hapten for hydroxyatrazine and melamine were diluted in coating carbonate buffer pH 9.6 were deposited in well defined locations. Thus, mixtures of a constant concentration of specific anti-hydroxyatrazine antibody and different concentration of hydroxyatrazine were prepared. Every solution was applied and incubated for one hour on coated areas. After washing and drying, tracer (goat anti-rabbit-Cy5) was applied by immersing the disc in a solution of PBST 10 mM, pH 7.5 with 1/64 solution of the original tracer. The incubation time was 1 hour. The support was then washed with water by spinning the disc at 1,000 rpm.

As is shown in FIG. 1, the melamine does not demonstrate any reaction with hydroxyatrazine reagents at any studied concentration. The competition principle worked very well with hydroxyatrazine. The FIG. 1 graphic shows a very good sensitivity to hydroxyatrazine.

EXAMPLE 3

An optical compact audiodisc was used to demonstrate an automated deposition. The following procedure was preformed to prepare and to coat the disc.

1. The disc was washed thoroughly with detergent, as described by Example 1.
2. Droplets of coating antigens were applied by the piezoelectric printing apparatus, described more fully hereinafter. Briefly, a three channel print head was used. Every channel was filled with a different coating solution. Using computer software (see Appendix A), the support surface was coated by producing separated circles of both conjugates. The antigens were in 50 mM carbonate buffer, pH 9.6 (30% ethylene glycol). Three rings were formed: the inner ring was coating antigen for hydroxyatrazine assay; the middle ring was coating antigen for carbaryl assay; and the outer ring was coating antigen for molinate assay.

3. The disc was stored at 100% moisture for 1 hour at room temperature, then washed with 100 mM phosphate buffered saline, pH 7.5 containing 0.05% Tween 20 (PBST).

4. The three rings were divided into 8 equal sectors with a black colored marker. The following mixtures of 50% volume, 100 µM analyte(s) plus 50% volume of 1/200 dilutions of rabbit polyclonal antibodies specific for hydroxyatrazine, carbaryl, and molinate, were applied. All reagents were dissolved in PBST. The disc was incubated at 100% moisture for 1 hour. The 8 sectors were:
   a. zero analytes
   b. hydroxyatrazine
   c. carbaryl
   d. molinate
   e. hydroxyatrazine, carbaryl
   f. hydroxyatrazine, molinate
   g. carbaryl, molinate
   h. hydroxyatrazine, carbaryl, molinate.

5. The disc was washed with PBST.

6. A solution of goat anti-rabbit IgG labeled with Cy5 fluorescent dye diluted 1/64 in PBST was added and the disc incubated at 100% moisture for 1 hour.

7. The disc was washed with PBST, and scanned with a fluorescence scanner.

Figure 2:
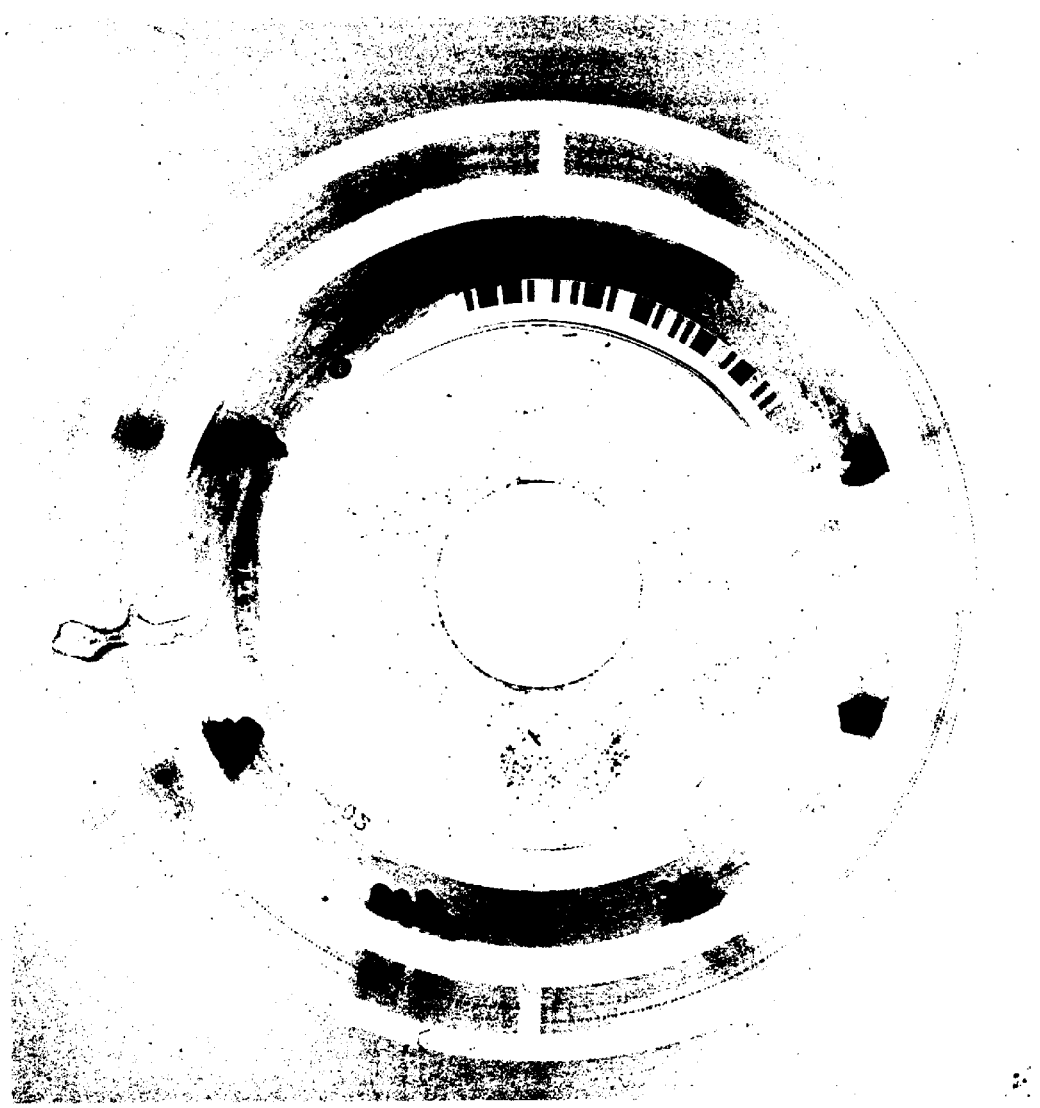
FIG. 2 is a plane illustration of a solid support embodiment of the invention having deposited thereon three different antigens.

Turning to FIG. 2, the figure shows a plane illustration of a solid support embodiment of the present invention having deposited thereon three different antigens. As shown in the figure, each of the three different antigens is represented by a dotted concentric ring appeared on the solid support surface. Each dot of the rings contains one droplet of the antigen to be reacted with the analytes. In this preferred embodiment as shown, each of the three rings were further divided into 8 equal sectors. Each sector is thereby applied with a different analyte for analysis as described in Example 3. The results can be illustrated by FIG. 3.

Figure 3:
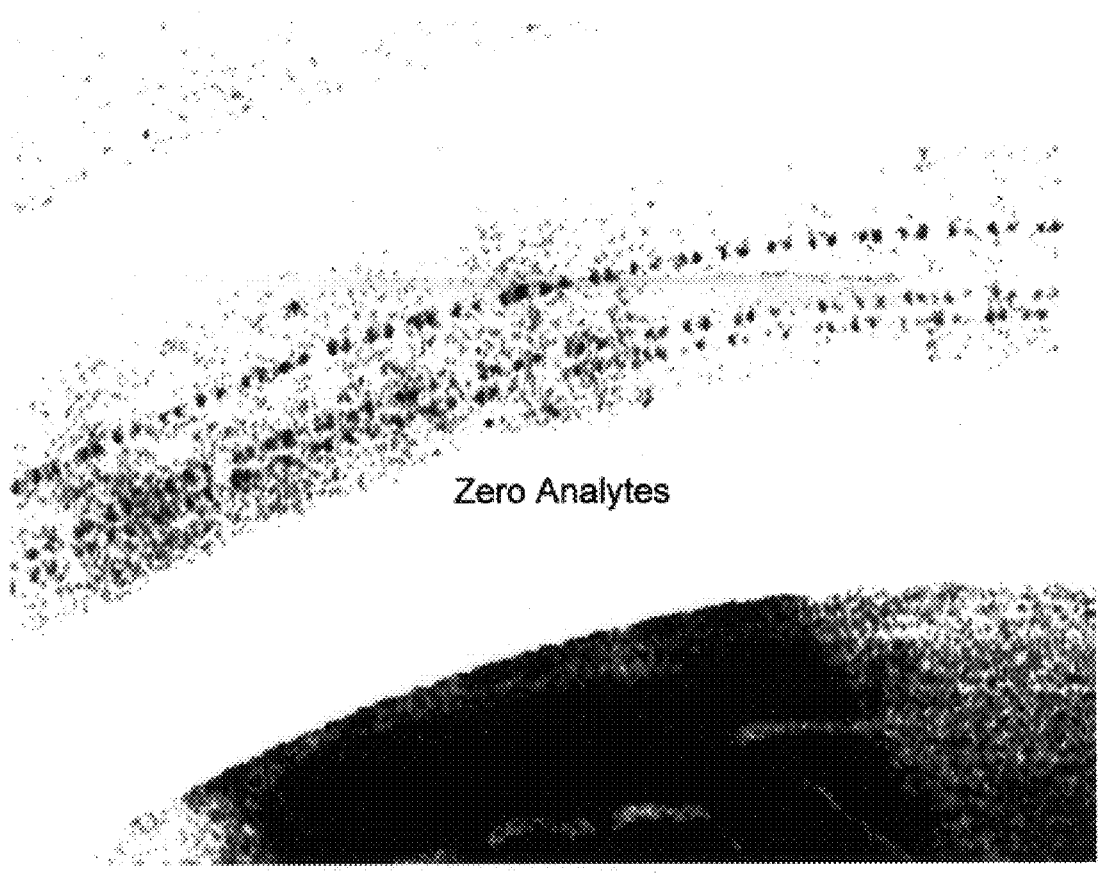
FIG. 3 is a fluorescent scan magnified nine times, taken from a portion of a solid support embodiment of the invention as illustrated by FIG. 2; and, FIG. 4 is a schematic diagram of a piezoelectric printing system.

FIG. 3 is a fluorescent scan magnified nine times, taken from a portion of a solid support embodiment of the invention as illustrated by FIG. 2. Because of the added fluorescers for the detection of the reactions between the antigens and the analytes, the results can be detected by a fluorescence scanner. Finally, the scanned results are inputted to a personal computer for storage and analysis.

EXAMPLE 4

In another embodiment of the present invention, the assay system of the present invention can be used with an enzyme label to catalyze the production of a colored precipitate. The specific steps may be as follows:

1. Apply droplets of protein-hapten conjugate to the disk support surface.
2. Wash the disk support surface.
3. Incubate the disk support with a mixture of analyte and primary antibody.
4. Wash the disk support surface again.
5. Incubate the disk support with a secondary antibody labeled with alkaline phosphatase.
6. Wash the disk support surface one more time.
7. Add a mixture of BCIP (i.e. 5-bromo-4-chloro-3-indoyl phosphate) and NBT (i.e. nitroblue tetrazolium) onto the disk support surface.
8. After a few minutes, the disk support surface can be scanned to detect precipitated colored product.

Figure 4:
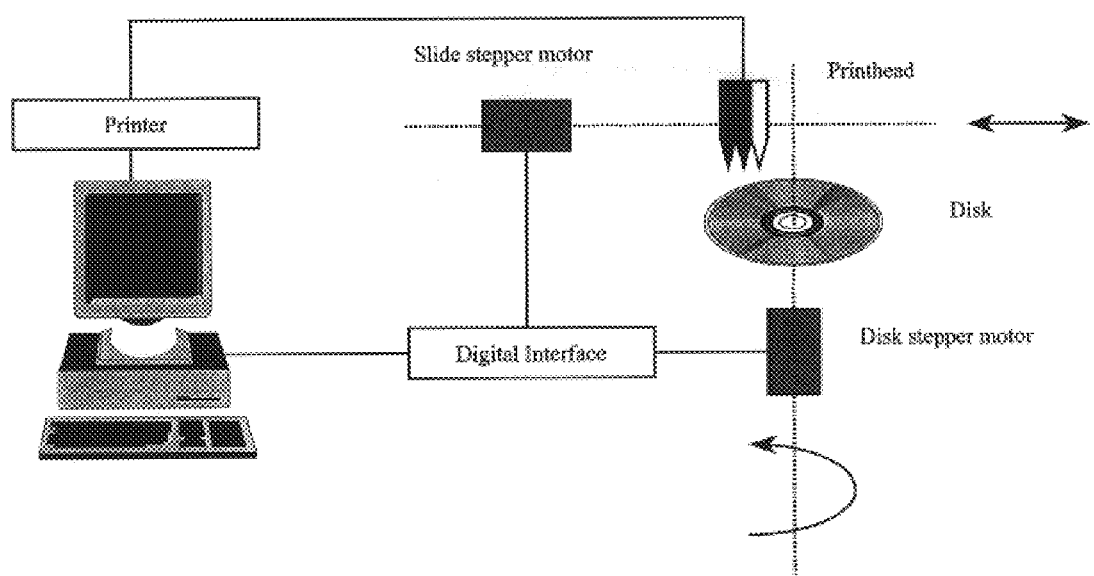

FIG. 4 shows a schematic diagram of a piezoelectric printing system 1 of the present invention. In the printing system as shown, the disk solid support 10 coated with immobilized anti-ligands is rotationally positioned by a disk stepper motor 20 controlled by a personal computer 30. A printhead 40 used for dispensing droplets of reagents onto the solid support surface 50 is connected to a slid stepper motor 60 for positioning the printhead 40 transversally over the support surface 50 to dispense at least one reagent on the support surface 50. The printhead 40 as shown in FIG. 4 comprises three piezoelectric heads 70a, 70b, and 70c. Each piezoelectric head is connected to a separate syringe cylinder (not shown) holding a different reagent. The position of the printhead 40 is also controlled by the personal computer 30 through the printer port 80 for accurate alignment over the solid support surface 50 so that the reagents can be applied to specific locations on the solid support surface 50 according to a predefined pattern.

It is to be understood that while the invention has been described above in conjunction with preferred specific embodiments, the description and examples are intended to illustrate and not limit the scope of the invention, which is defined by the scope of the appended claims.

APPENDIX A

```
'****************************************************
'*  Program:      8.BAS                              *
'*  Description:  Program for printing onto a CD     *
'*  Revision:     1.00                               *
'****************************************************
'
'Declare escape sequences
LET MAGENTA$ = CHR$(27) + CHR$(114) + CHR$(1)
LET CYAN$ = CHR$(27) + CHR$(114) + CHR$(2)
LET YELLOW$ = CHR$(27) + CHR$(114) + CHR$(4)
LET HDOT$ = CHR$(27) + CHR$(42) + CHR$(40) + CHR$(1) + CHR$(0) +
CHR$(128) + CHR$(0) + CHR$(0)
LET mdot$ = CHR$(27) + CHR$(42) + CHR$(40) + CHR$(1) + CHR$(0) +
CHR$(128) + CHR$(0) + CHR$(0)
LET LDOT$ = CHR$(27) + CHR$(42) + CHR$(40) + CHR$(1) + CHR$(0) +
CHR$(128) + CHR$(0) + CHR$(0)
LET SMALLDOT$ = CHR$(27) + CHR$(40) + CHR$(101) + CHR$(2) +
CHR$(0) + CHR$(1)
LET LINESPACE$ = CHR$(27) + CHR$(43) + CHR$(1) 'Set 1/360-inch line
spacing
```

APPENDIX A-continued

```
,
OPEN "lpt1" FOR OUTPUT AS #2 'Open gateway to printer on lpt1
,
PRINT #2, SMALLDOT$ 'Set small dot size mode
PRINT #2, LINESPACE$
,
FOR I = 1 TO 3 'Loop to print dot set on I*(360/618)ø
    OUT 557, 8
    OUT 557, 0
    PRINT #2, MAGENTA$; HDOT$; CYAN$; mdot$; YELLOW$; LDOT$
    TIME$ = "00:00:00"
    DO WHILE TIME < 4 'Time loop to delay print time
    CLS
    PRINT "Cycles completed"; I
    LOOP
NEXT
,
CLOSE #2 'Close gateway to printer
END
```

What is claimed is:

1. An assay method, comprising:

providing a solid support with opposed sides, one of which is an informational surface, the solid support having one or more capture binding agents immobilized on one side, each capture binding agent having a binding specificity for an analyte of interest;

contacting the capture binding agents with a liquid sample in which one or more analytes may be present;

separating the liquid sample from the solid support;

incubating the capture binding agents with a developing agent, the developing agent capable of binding with analyte when bound to the capture binding agent, the developing agent including an optical marker, wherein the optical marker generates an optical signal in proportion to bound analytes;

detecting the optical signal; and, recording onto the informational surface on the other side of the solid support information concerning the optical signal.

2. The assay method as in claim 1 wherein the optical signal is in analog form.

3. The assay method as in claim 1 wherein the information recorded onto the solid support is in digital form.

4. The assay method as in claim 1 wherein the information recorded onto information surface is via a plurality of microscopic pit and land formations.

* * * * *

UNITED STATES PATENT AND TRADEMARK OFFICE
CERTIFICATE OF CORRECTION

PATENT NO.    : 6,342,395 B1
DATED         : January 29, 2002
INVENTOR(S)   : Hammock et al.

It is certified that error appears in the above-identified patent and that said Letters Patent is hereby corrected as shown below:

<u>Title page,</u>
Item [73], "Assignee: The Regents of the University of California (Oakland,CA)" it should read -- Assignees: The Regents of the University of California (Oakland, CA)" and Universidad Politecnica de Valencia (Valencia, Spain) --

Signed and Sealed this

Twenty-fourth Day of December, 2002

JAMES E. ROGAN
*Director of the United States Patent and Trademark Office*